United States Patent
Stovall, Jr.

(10) Patent No.: US 12,293,834 B2
(45) Date of Patent: May 6, 2025

(54) INTERACTIVE MEDICAL COMMUNICATION DEVICE

(71) Applicant: Legacy Innovative Technologies, LLC, Halfmoon, NY (US)

(72) Inventor: Sherman S. Stovall, Jr., Halfmoon, NY (US)

(73) Assignee: LEGACY INNOVATIVE TECHNOLOGIES LLC, Halfmoon, NY (US)

( * ) Notice: Subject to any disclaimer, the term of this patent is extended or adjusted under 35 U.S.C. 154(b) by 0 days.

(21) Appl. No.: 18/093,664

(22) Filed: Jan. 5, 2023

(65) Prior Publication Data
US 2024/0233940 A1    Jul. 11, 2024

(51) Int. Cl.
| | |
|---|---|
| *G16H 50/20* | (2018.01) |
| *A61B 5/00* | (2006.01) |
| *A61B 90/00* | (2016.01) |
| *G16H 20/30* | (2018.01) |
| *G16H 80/00* | (2018.01) |

(52) U.S. Cl.
CPC .......... *G16H 50/20* (2018.01); *A61B 5/6803* (2013.01); *A61B 90/36* (2016.02); *G16H 20/30* (2018.01); *G16H 80/00* (2018.01); *A61B 2090/365* (2016.02)

(58) Field of Classification Search
CPC . A61B 2090/365; A61B 5/6803; A61B 90/36; G16H 20/30; G16H 80/00
USPC .......................................................... 600/301
See application file for complete search history.

(56) References Cited

U.S. PATENT DOCUMENTS

| | | | |
|---|---|---|---|
| 8,968,195 B2 | 3/2015 | Tran | |
| 10,310,296 B2* | 6/2019 | Howell | .................. G02C 11/10 |
| 10,594,757 B1* | 3/2020 | Shevchenko | ........... G10L 15/22 |
| 10,691,407 B2* | 6/2020 | Yoo | ......................... G10L 15/02 |
| 10,813,619 B2 | 10/2020 | Samec et al. | |

(Continued)

FOREIGN PATENT DOCUMENTS

| | | | | |
|---|---|---|---|---|
| CA | 2895778 C | * | 10/2021 | ............. G06T 11/00 |
| CN | 105842879 A | * | 8/2016 | |

(Continued)

OTHER PUBLICATIONS

"Facilitating Healthcare Delivery with Vuzix Smart Glasses," White Paper 2020, vuzix.com. https://www.vuzix.com/pages/the-power-of-ar-smart-glasses-in-telemedicine [Date accessed: Jan. 10, 2022].

*Primary Examiner* — Michael J Lau
(74) *Attorney, Agent, or Firm* — Bold IP PLLC; Houda El-Jarrah

(57) ABSTRACT

An interactive medical communication device is disclosed. The device implements multiple modes including an environmental diagnostics mode configured to detect conditions and potential hazards in an area around a user of the device; a virtual assistant mode configured to provide guidance, encouragement, education, mental health treatment, and decision-making assistance to the user; an area scanning mode configured to analyze and provide information to the user about objects in a field of vision of the user; a telehealth mode configured to connect the user to a preferred wellness provider or to a recommended wellness provider; and a vitals diagnostics mode configured to measure the vitals of the user and to contact medical assistance if needed.

17 Claims, 7 Drawing Sheets

(56) References Cited

U.S. PATENT DOCUMENTS

| | | |
|---|---|---|
| 10,842,967 B2 | 11/2020 | Liu |
| 10,910,016 B2 | 2/2021 | Rothschild et al. |
| 10,945,641 B2 | 3/2021 | Mirelman et al. |
| 2005/0228236 A1* | 10/2005 | Diederich .............. G10L 17/26 128/920 |
| 2007/0271298 A1* | 11/2007 | Juang .................... G16H 40/67 |
| 2012/0206334 A1 | 8/2012 | Osterhout et al. |
| 2013/0085758 A1* | 4/2013 | Csoma .................. G16H 40/67 704/270.1 |
| 2014/0145915 A1 | 5/2014 | Ribble et al. |
| 2014/0222719 A1* | 8/2014 | Poulin ..................... G16Z 99/00 706/46 |
| 2014/0257855 A1* | 9/2014 | Moore .................. G16H 40/67 705/2 |
| 2015/0088547 A1 | 3/2015 | Balram et al. |
| 2016/0188799 A1* | 6/2016 | Borras .................... H04N 7/15 434/428 |
| 2016/0270656 A1* | 9/2016 | Samec ................ A61B 3/0025 |
| 2016/0324478 A1* | 11/2016 | Goldstein .............. A61B 5/11 |
| 2018/0025303 A1* | 1/2018 | Janz ...................... G16H 50/20 705/2 |
| 2018/0039752 A1 | 2/2018 | Subbarao et al. |
| 2018/0132776 A1* | 5/2018 | Flickinger ............... A63F 13/25 |
| 2018/0226158 A1* | 8/2018 | Fish ..................... A61B 5/0022 |
| 2018/0276895 A1 | 9/2018 | Hodge |
| 2019/0074093 A1* | 3/2019 | Walsh .................... G16H 10/20 |
| 2019/0272516 A1* | 9/2019 | Rheault .................... G07F 9/10 |
| 2019/0275332 A1* | 9/2019 | Cedeno ............. A61N 1/36139 |
| 2019/0278110 A1* | 9/2019 | Howell .................... G02C 5/14 |
| 2019/0355351 A1* | 11/2019 | Kim ........................ G10L 15/22 |
| 2019/0385342 A1* | 12/2019 | Freeman ................. G06T 11/00 |
| 2020/0000401 A1 | 1/2020 | Dullen |
| 2020/0286603 A1* | 9/2020 | Ajilore .................... G16H 20/70 |
| 2021/0096726 A1* | 4/2021 | Faulkner ............. G06F 3/04842 |
| 2021/0097883 A1* | 4/2021 | Scott ...................... G06N 20/00 |
| 2021/0195732 A1* | 6/2021 | Longinotti-Buitoni ...................... H05K 3/361 |
| 2021/0319895 A1* | 10/2021 | Joao ...................... G06F 16/182 |
| 2021/0392974 A1* | 12/2021 | van der Hoeven .... A62B 23/02 |
| 2022/0059122 A1* | 2/2022 | Xiu ........................ G10L 17/04 |
| 2022/0061767 A1* | 3/2022 | Goldstein .......... A61B 5/14542 |
| 2022/0230740 A1* | 7/2022 | Ryu ...................... G06F 16/9017 |
| 2022/0254019 A1* | 8/2022 | Connor .................. G16H 40/67 |
| 2022/0261817 A1* | 8/2022 | Ferrucci ................. G16H 70/20 |
| 2022/0286625 A1* | 9/2022 | Afrasiabi ............... H04N 7/147 |
| 2023/0098614 A1* | 3/2023 | Valles Leon ........... G16H 40/67 705/2 |

FOREIGN PATENT DOCUMENTS

| | | | | |
|---|---|---|---|---|
| CN | 106845120 A | | 6/2017 | |
| CN | 214375645 U | * | 10/2021 | |
| CN | 114080800 A | * | 2/2022 | .......... G02B 27/017 |
| CN | 114397773 A | * | 4/2022 | |
| CN | 114531951 A | * | 5/2022 | |
| CN | 114879366 A | * | 8/2022 | |
| CN | 114903429 A | * | 8/2022 | |
| CN | 217739931 U | * | 11/2022 | |
| DE | DD-284291 A5 | * | 11/1990 | |
| ES | 2441946 T3 | * | 2/2014 | .............. A61F 2/16 |
| GB | 2594852 A | * | 11/2021 | ......... A63B 24/0006 |
| JP | 2022102696 A | * | 7/2022 | |
| KR | 20170060761 A | | 6/2017 | |
| RU | 2005103883 A | * | 7/2006 | |
| RU | 2303969 C2 | * | 8/2007 | |

* cited by examiner

INTERACTIVE MEDICAL COMMUNICATION DEVICE

FIELD OF THE DISCLOSURE

This disclosure relates generally to communications between patients and their wellness providers, and more particularly to an interactive medical communication device.

BACKGROUND

The use of technology to improve patient care, reduce costs, and increase the effectiveness of wellness providers is of great interest. In recent years, wellness providers and patients have conducted their communications remotely rather than in person with increasing frequency. Known forms of remote communication between wellness providers and patients, however, typically require the use of a mobile phone, tablet, desktop computer, or other device that may be overly burdensome to the patient and/or ineffective for the wellness provider. Devices such as mobile phones, tablets and computers do not allow the hands of the wellness provider or the patient to be free. A need exists for a less burdensome and more effective means for remote communication between wellness provider and patient.

SUMMARY

One aspect of this disclosure is an interactive medical communication device. In one implementation, the device takes the form of interactive medical glasses providing an augmented or virtual reality environment to facilitate seamless two-way communication between patient and doctor. The device implements multiple interactive medical communications modes including an environmental diagnostics mode that detects conditions and potential hazards in an area around a user of the device; a virtual assistant mode that provides guidance, encouragement, education, mental health treatment, and decision-making assistance to the user; an area scanning mode that analyzes and provides information to the user about objects in a field of vision of the user; a telehealth mode that connects the user to a preferred wellness provider or to a recommended wellness provider; and a vitals diagnostics mode that measures the vitals of the user and summons medical assistance if needed. In one implementation, the virtual assistant mode is configured to listen to the keywords and syntax of the user; and determine the user's state of mind and thought management process from the keywords and syntax of the user.

These and other aspects and advantages of this disclosure will be apparent from the following description and appended claims.

BRIEF DESCRIPTION OF THE DRAWINGS

Embodiments of the invention are described in detail below with reference to the following drawings. The drawings are for illustrative purposes only of selected embodiments, do not show all possible implementations, and are not intended to limit the scope of this description.

DETAILED DESCRIPTION

Figure 1:
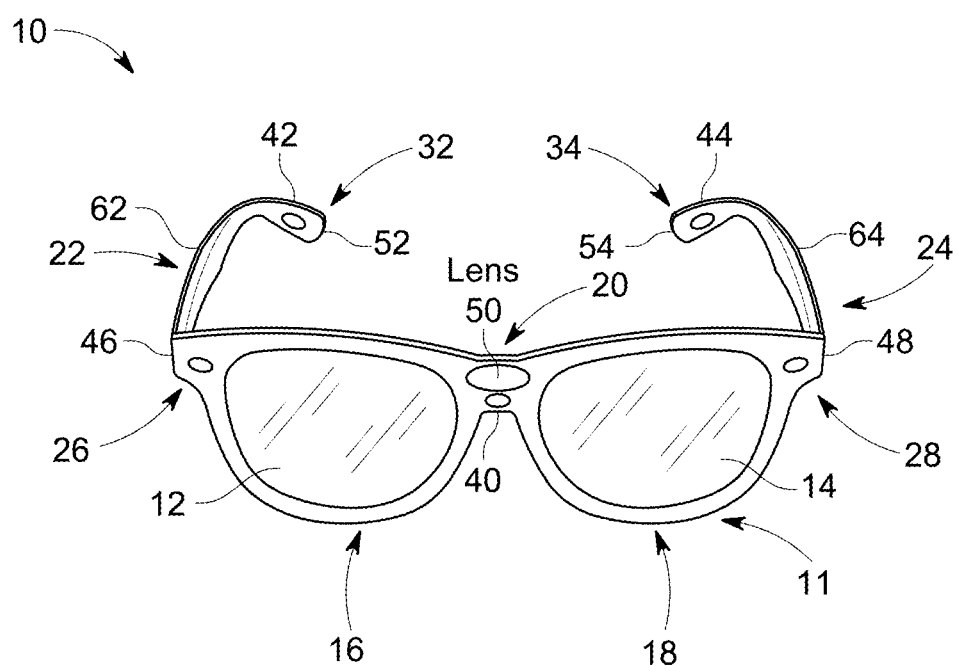
FIG. 1 is a conceptual block diagram of an interactive medical communication device, according to this disclosure.

FIG. 1 is a conceptual diagram of interactive medical communication device 10, according to this disclosure. In one non-limiting example, interactive medical communication device 10 resembles a pair of eyeglasses and is configured to display information, digital representations, images and/or videos directly in the user's field of vision in the form of an augmented reality (AR) overlay. An interactive virtual assistant may be displayed in the user's field of vision that is configured to provide guidance, encouragement, education, mental health treatment, and decision-making assistance to the user. Device 10 is configured with sensors to measure and monitor a user's vital signs, and to measure and monitor conditions and potential hazards in the environment around the user.

Device 10 includes a display system comprising right ("sigma") camera lens 12 and left ("omega") camera lens 14 held within and supported by frame 11. Frame 11 may be constructed from any suitable material, such as (without limitation) plastic, metal, other materials, or a combination thereof, and is suitably formed to house various components and circuitry for providing interactive medical communications, as described in more detail below. Right ("sigma") lens 12 is held by right rim 16 of frame 11 and left ("omega") lens 14 is held by left rim 18 of frame 11. Lenses 12, 14 and rims 16, 18 may be round, square, oval, or any other desired shape. Rims 16 and 18 are connected by bridge 20. Right temple or arm 22 is joined by right hinge 26 to right rim 16, and left temple or arm 24 is joined by left hinge 28 to left rim 18. Right temple 22 extends from right hinge 26 to right temple tip 32, and left temple 24 extends from left hinge 28 to left temple tip 34. Temples 22, 24 and tips 32, 34 may vary in length and shape and, when worn, temples 22 and 24 stretch back to rest over a user's ears, and temple tips 32, 34 fit behind the user's ears. As will be described in more detail below, a processor(s) or central processing unit(s) is disposed in temples 22, 24 and configured to execute instructions to perform the various functions of device 10.

Various components for providing interactive medical communications are integrated into interactive medical communications device 10. Lenses 12 and 14 of the display system are special camera lenses positioned in front of the eyes of the user. Lenses 12 and 14 work in concert with trans-focal camera lens 50 configured in bridge 20 to provide multiple functions. Lenses 12, 14 and 50 are configured to facilitate projection of a digitized display of another person, object, image, or video recording into an augmented or virtual reality digital space in front of the user's eyes. This may be, for example, a prerecorded video or image, a digitized virtual assistant or avatar as described below, or may be a digital representation of another user of another interactive medical communication device that is in communication with device 10, thereby providing live "FaceTime" style video conference ability without the use of a mobile device or smart phone.

Creation of the digitized display in front of the user's eyes may be accomplished in a number of different ways. In one implementation, a mini projector configured in device 10 is configured to project images onto semi-transparent prisms located near hinges 26, 28, which in turn reflect the projector's image onto the user's retina or onto lenses 12, 14. In another implementation, a holographic element embedded in some or all of lenses 12, 14, 50 is configured to redirect light onto the retinas to create an image or video. In another implementation, a transparent display(s) is integrated into the lenses.

Lenses 12, 14 and 50 are also configured to capture the image of the user of device 10 by digitally scanning and capturing the user's image, which may then be projected onto the augmented or virtual reality digital space of another interactive medical communication device, or onto a predetermined digital background. The prisms situated near hinges 26, 28 help to capture, redirect, and focus light (simultaneously scan and reflect light) so that the user's face can be scanned/captured and re-projected onto a virtual or digital background of another device. Lenses 12, 14 and 50 are also capable of capturing images and video recordings of objects in the user's field of view and storing those images and video recordings in memory for later retrieval and viewing. Trans-focal lens 50 also has the capability to target objects in its field of view.

Device 10 comprises various components and devices that allow user input. Bridge button/input device ("delta link") 40 is configured in bridge 20. Right temple button/input device ("alpha link") 42 is configured in right temple tip 32. Left temple button/input device ("beta link") 44 is configured in left temple tip 34. Right hinge button/input device ("sigma link") 46 is configured in right rim 16 adjacent to right hinge 26. Left hinge button/input device ("omega link") 48 is configured in left rim 18 adjacent to left hinge 28. Device 10 further comprises a microphone for capturing the user's voice, audio input, and/or ambient sounds in the user's environment.

Though described as buttons, input devices 40, 42, 44, 46 and 48 may take any other suitable forms that allow actuation of the underlying function. For example, and without limitation, user input could instead be facilitated by touchpads or touch sensors, voice commands via the microphone (speech recognition), gesture recognition, eye/facial movements captured by the camera lenses, or by remote control via a smartphone or other device. Moreover, though a particular arrangement of user input devices has been described, this description is merely exemplary and may take many other forms. The user input devices may be provided in different locations than those described above and may be provided in greater or fewer numbers. Functions provided by multiple buttons may be consolidated into fewer buttons, for example, and functions provided by a single button may be spread over multiple buttons.

Right ear speaker (audio output device) 52 is configured in right temple tip 32, and left ear speaker (audio output device) 54 is configured in left temple tip 34, thereby providing the user with the ability to hear live or prerecorded audio. In one implementation, speakers 52 and 54 do not enter the user's ears, rather, the speakers are situated in temple tips 32, 34, and emit audio at a volume sufficient for the user to hear. Though a particular arrangement of audio output devices has been described, this description is merely exemplary and may take many other forms. Audio output devices may be provided in different locations than those described above and may be provided in greater or fewer numbers. Moreover, the audio output devices may take other suitable forms, such as earbuds or headphones that are coupled to device 10 via a wired or wireless connection. As an alternative to speakers, sound may be transferred to the cochlea (ear bone) via bone conduction rather than through the air. That is, vibrations may be transferred from frame 11 to the cochlea via the cranium, bypassing the eardrum.

Right ("mu") sensor 62 is configured in right temple 22 and left ("nu") sensor 64 is configured in left temple 24. Sensors 62 and 64 are configured to detect and assess various diagnostic data about the user (such as the user's vitals) and the user's environment (temperature, etc.) Sensors 62, 64 may comprise, for non-limiting purposes of illustration, a gyroscope, an accelerometer, a magnetometer, optical sensors, a thermometer, a GPS unit, a blood glucose monitor, a blood pressure monitor, pulse rate monitor, electrocardiograph (ECG) monitor, respiration monitor, etc. Though a particular arrangement of sensors has been described, this description is merely exemplary and may take many other forms. Sensors may be provided in different locations than those described above and may be provided in greater or fewer numbers.

The various components of device 10 described above work together to provide various modes, methods, or functions for interactive medical communication. These functions include, without limitation, an environmental diagnostics mode 200 (FIG. 2); a virtual assistant (VA) mode 300 (FIG. 3); an area scan mode 400 (FIG. 4); a telehealth mode 500 (FIG. 5); and a vitals diagnostic mode 600 (FIG. 6).

Figure 2:
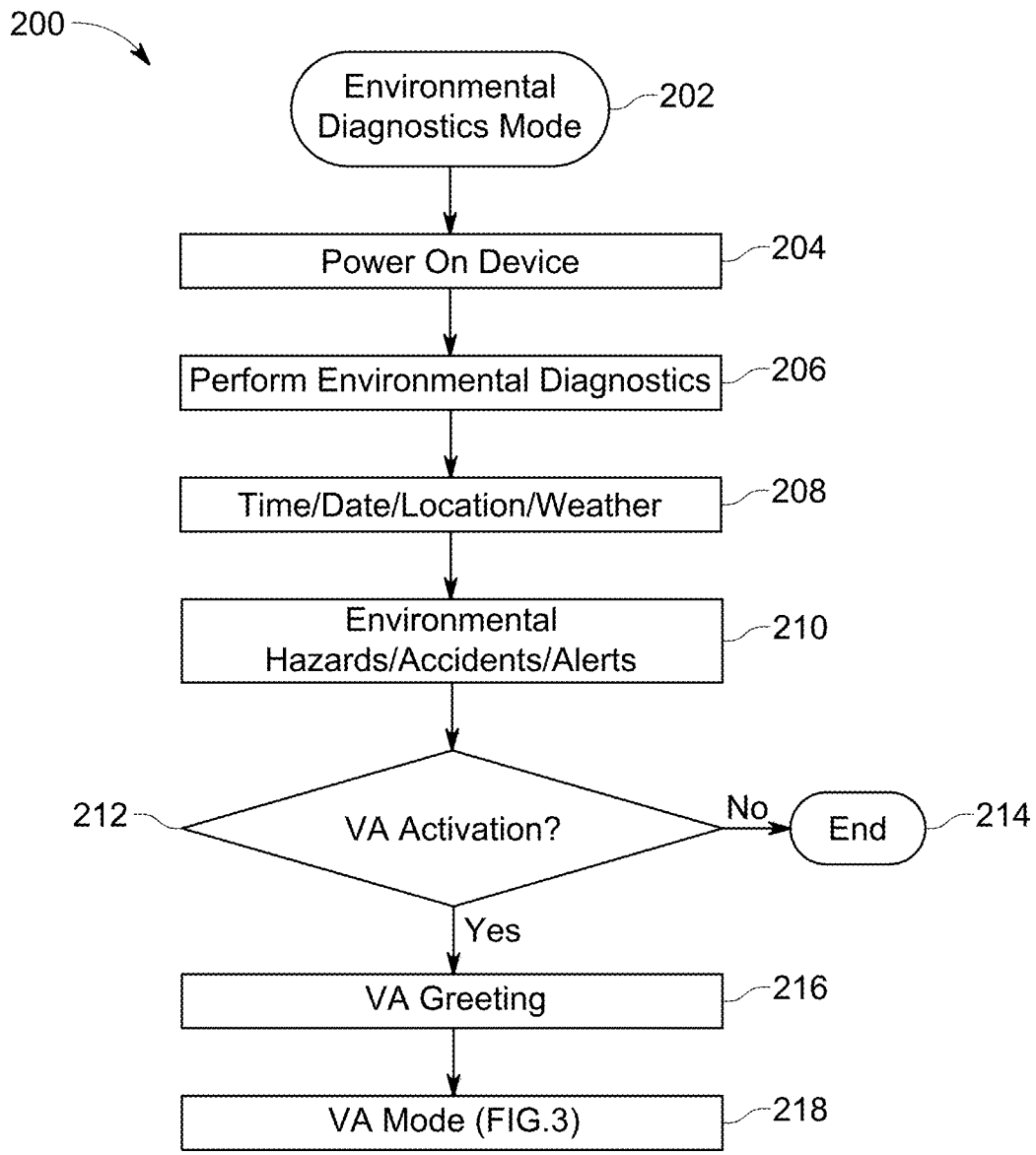
FIG. 2 is a flow chart illustrating an environmental diagnostics mode of the interactive medical communication device of FIG. 1, according to this disclosure.

FIG. 2 is a flow chart illustrating environmental diagnostics mode 200 of interactive medical communication device 10, according to this disclosure. Environmental diagnostics mode 200 detects and analyzes conditions in an area around a user of device 10 based on, for example, data provided by sensors 62, 64. In one non-limiting example, environmental diagnostics mode 200 is initiated in step 202 by actuation of right temple button 42 ("alpha link"). Environmental diagnostics mode 200 may alternatively be linked to from other operation modes of device 10, such as from area scan mode 400 (FIG. 4; step 418) or from vitals diagnostics mode 600 (FIG. 6; step 622).

Button 42 may be operated to power on device 10, for example by being pressed continuously for a predetermined period, such as two seconds (step 204). In step 206, button 42 may be operated to initiate environmental diagnostics, for example, by being pressed three times in rapid succession. Environmental diagnostics may include, without limitation, obtaining date, location, weather, coordinates, or conducting a place of interest (POI) search (step 208). This information may be obtained, for example, via data gathered by sensors 62, 64 and/or via a connection of device 10 to the Internet.

Environmental diagnostic mode 200 detects and analyzes conditions and hazards in an area around the user and may include detecting any potential hazards or conditions in the environment, such as toxic levels of carbon dioxide and/or other hazardous chemicals or materials (step 210). Based on the detected conditions, appropriate notifications, alerts, and assistance may be provided to the user. Where an environmental hazard or condition is detected, if the virtual assistant function has been activated (212-Yes), a virtual assistant or avatar is summoned and displayed on lenses 12 and 14 to provide a greeting and to provide warnings and information to the user regarding the hazard or condition (step 216). Then, in step 218, the method proceeds to the virtual assistant mode of FIG. 3. If the virtual assistant has not been activated (212-No), the environmental diagnostics mode ends (step 214).

Environmental diagnostic mode 200 may also comprise a navigation mode to assist the user in navigating their environment. Upon initiation of the navigation mode, if the virtual assistant function has been activated (212-Yes), the virtual assistant or avatar is summoned and displayed on lenses 12 and 14 to provide navigation instructions to the user, such as by voice command, to a desired location.

Figure 3:
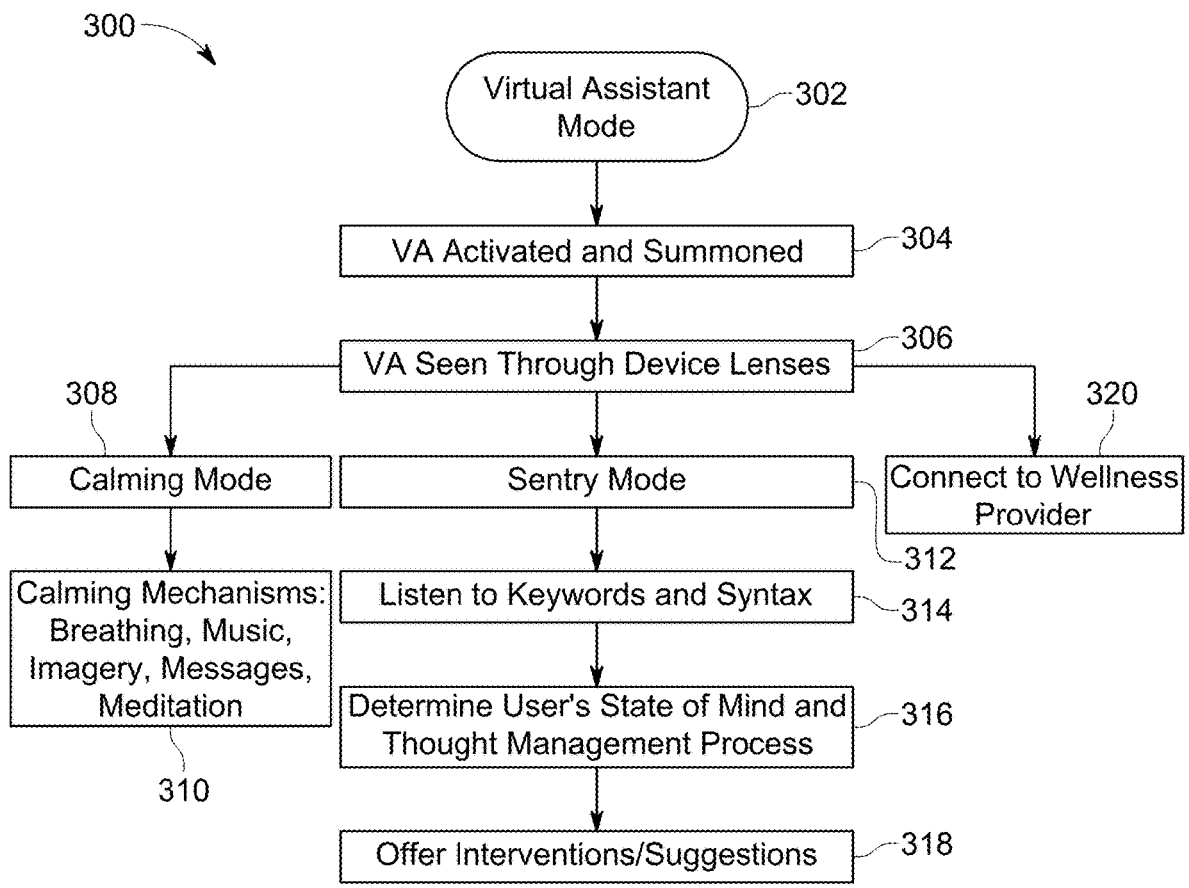
FIG. 3 is a flow chart illustrating a virtual assistant (VA) mode of the interactive medical communication device of FIG. 1, according to this disclosure.

FIG. 3 is a flow chart illustrating virtual assistant mode 300 of interactive medical communication device 10, according to this disclosure. In one non-limiting example, virtual assistant mode 300 is initiated in step 302 by actuation of left temple button 44 ("beta link"). Virtual assistant mode 300 may alternatively be linked to from other operation modes of device 10, such as from environmental diagnostics mode 200 (FIG. 2; step 218); area scan mode 400 (FIG. 4; step 418); or from vitals diagnostics mode 600 (FIG. 6; step 624).

In step 304, the virtual assistant is activated and summoned. The virtual assistant can be seen through lenses 12, 14 and can engage in seamless two-way communication with the user of device 10 in step 306. Lenses 12 and 14 provide an augmented or virtual reality digital space within which a display of the virtual assistant is projected. The virtual assistant is configured to provide assistance to the user such as, without limitation, guidance, encouragement, education, mental health treatment, and decision-making assistance.

The virtual assistant may, for example, enter a calming mode 308. In calming mode 308, the virtual assistant may provide various calming mechanisms such as breathing exercise/control, playing music, activated guided imagery, meditation, and/or playing calming, pre-recorded messages (step 310). Device 10 may also be synched to the user's cell phone, for example, to play appropriate music in calming mode 308. Further in this regard, the synch between device 10 and the user's cell phone may be used to play user-chosen music at any time of the user's choice, apart from suggestions from calming mode 308.

Alternatively, or in addition, the virtual assistant may enter sentry mode 312. In sentry mode 312, the virtual assistant listens to the keywords and syntax of the user (step 314), as spoken by the user into the microphone of device 10 for example. From the user's keywords and syntax, the virtual assistant of device 10 is configured to determine the user's state of mind and thought management process (step 316) and may offer interventions/suggestions based on the user's determined state of mind and thought management process (step 318). The virtual assistant may offer support, for example, by reminding the user to be aware of their thoughts. The user's facial expressions may also be considered and analyzed by the virtual assistant in determining the user's state of mind.

The virtual assistant, if appropriate, may also offer assistance in step 320 by connecting the user to the user's preferred wellness provider, or by connecting the user with a network of potential wellness providers and support givers. The user may connect to a network of wellness providers and support givers in real time for support. In one implementation, digital images/videos of available wellness providers and support givers may be projected into an augmented or virtual reality "room", with the virtual assistant available to introduce the user to those present in the virtual room.

The virtual assistant may also assist in navigating the user through the various modes of device 10, such as environmental diagnostics mode 200 (FIG. 2); area scan mode 400 (FIG. 4); telehealth mode 500 (FIG. 5); vitals diagnostic mode 600 (FIG. 6); and any other mode employed by device 10. The virtual assistant may also provide tutorials on the use of device 10, as well as assistance in making or changing the settings of device 10.

Figure 4:
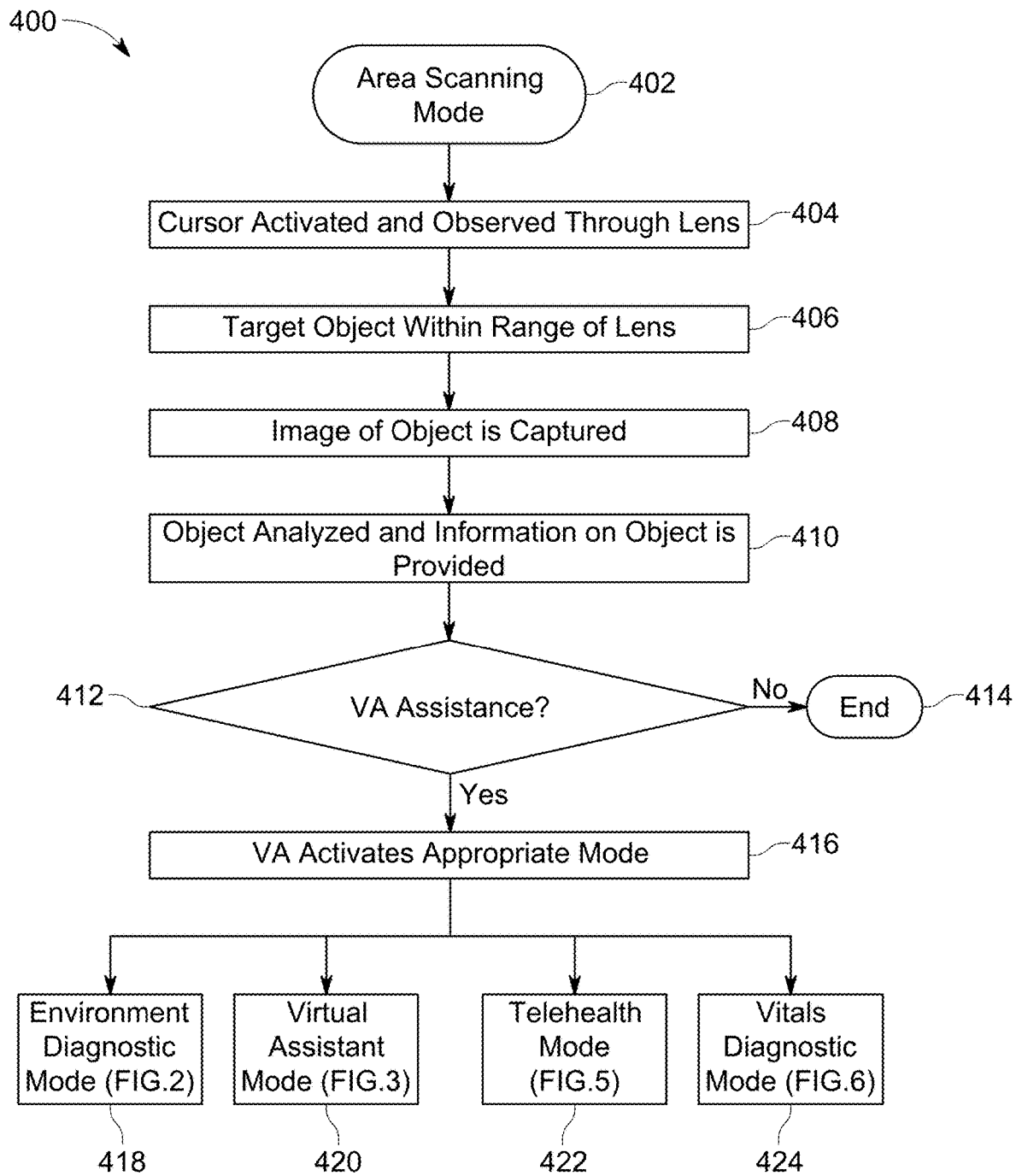
FIG. 4 is a flow chart illustrating an area scanning mode of the interactive medical communication device of FIG. 1, according to this disclosure.

FIG. 4 is a flow chart illustrating area scanning mode 400 of interactive medical communication device 10, according to this disclosure. In one non-limiting example, area scanning mode 400 is initiated in step 402 by actuation of right hinge button 46 ("sigma link"). Area scanning mode 400 may alternatively be linked to from other operation modes of device 10, such as from vitals diagnostics mode 600 (FIG. 6; step 626).

Area scanning mode 400 provides area scanning and object identification capabilities. In step 404, a cursor is activated that can be observed through at least one of lenses 12, 14. In one non-limiting example, the cursor is observed through right camera ("sigma") lens 12. Lens 12 is configured to target objects that are within view and within range of lens 12 (step 406). In one non-limiting example, the range of lens 12 is about five meters. Lens 12 focuses light on the selected object, and in step 408 the user captures an image of the object, such as by pressing button 46. The image of the object is analyzed and information on the object is presented to the user (step 410). Information on images of captured objects may be obtained, for example, by uploading the captured image of the object to the Internet.

In addition, the virtual assistant may provide appropriate assistance based on the scan of the user's environment and the objects in that environment. If the user wishes virtual assistance in this regard (step 412-Yes), based on the results of the area scan, the virtual assistant activates the appropriate operational mode (step 416). The navigation mode of environmental diagnostics mode 200, for example, may also be incorporated into area scanning mode 400. Depending on the results of the scan, the virtual assistant may activate environmental diagnostics mode 200 (step 418); virtual assistant mode 300 (step 420); telehealth mode 500 (step 422); or vitals diagnostics mode 600 (step 424).

Area scanning mode 400 may also include a feature by which the visual field of the user is continuously recorded, including video and/or audio, such that the user's experiences and effectively their life is being recorded and stored. In one implementation, the user can cast what they are seeing to others or to social media, such that others can experience the user's life through the user's eyes. This visual field recording and casting feature may be provided in area scanning mode 400 or may be provided in another appropriate mode or a separate mode.

Figure 5:
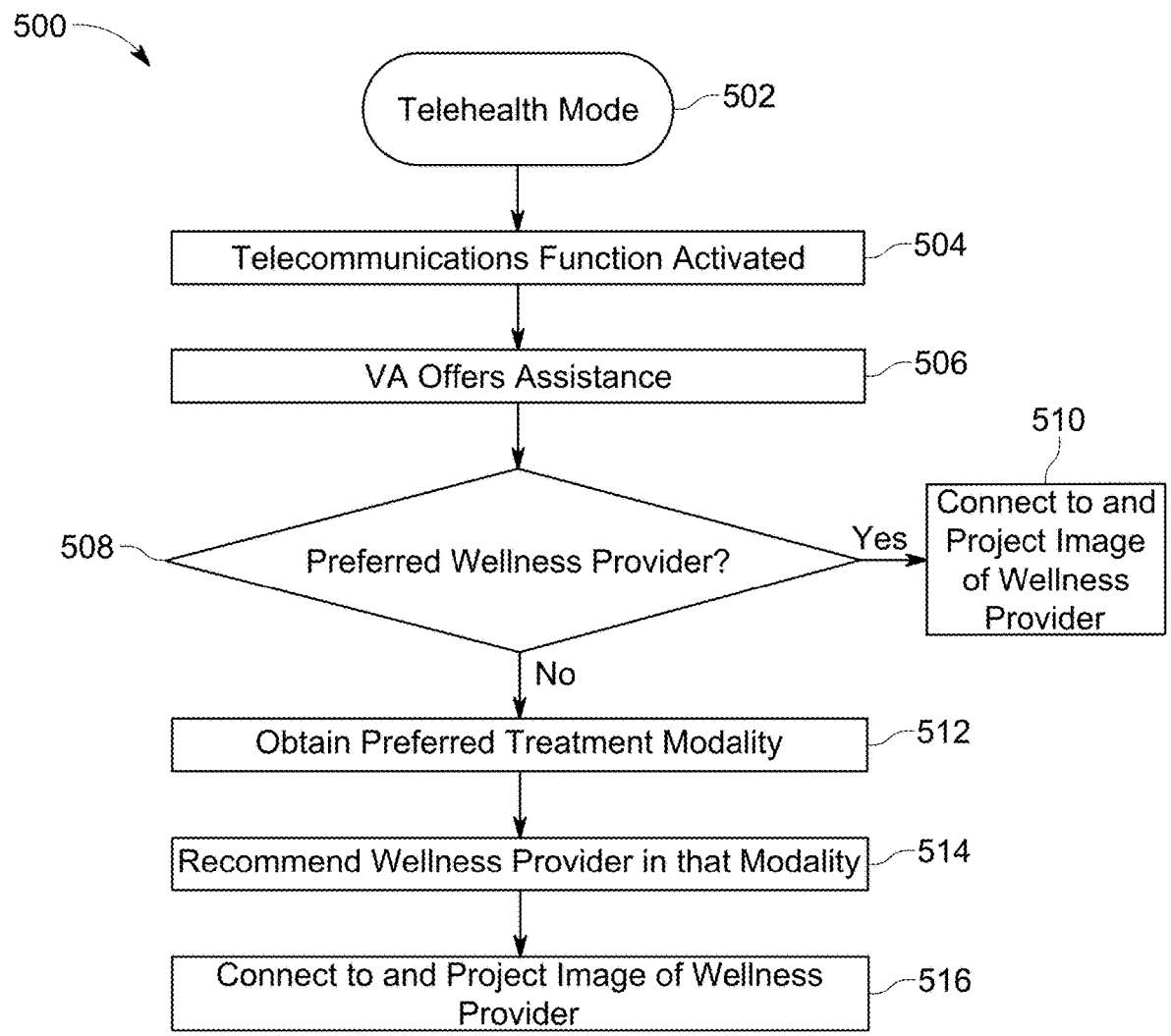
FIG. 5 is a flow chart illustrating a telehealth mode of the interactive medical communication device of FIG. 1, according to this disclosure.
Figure 6:
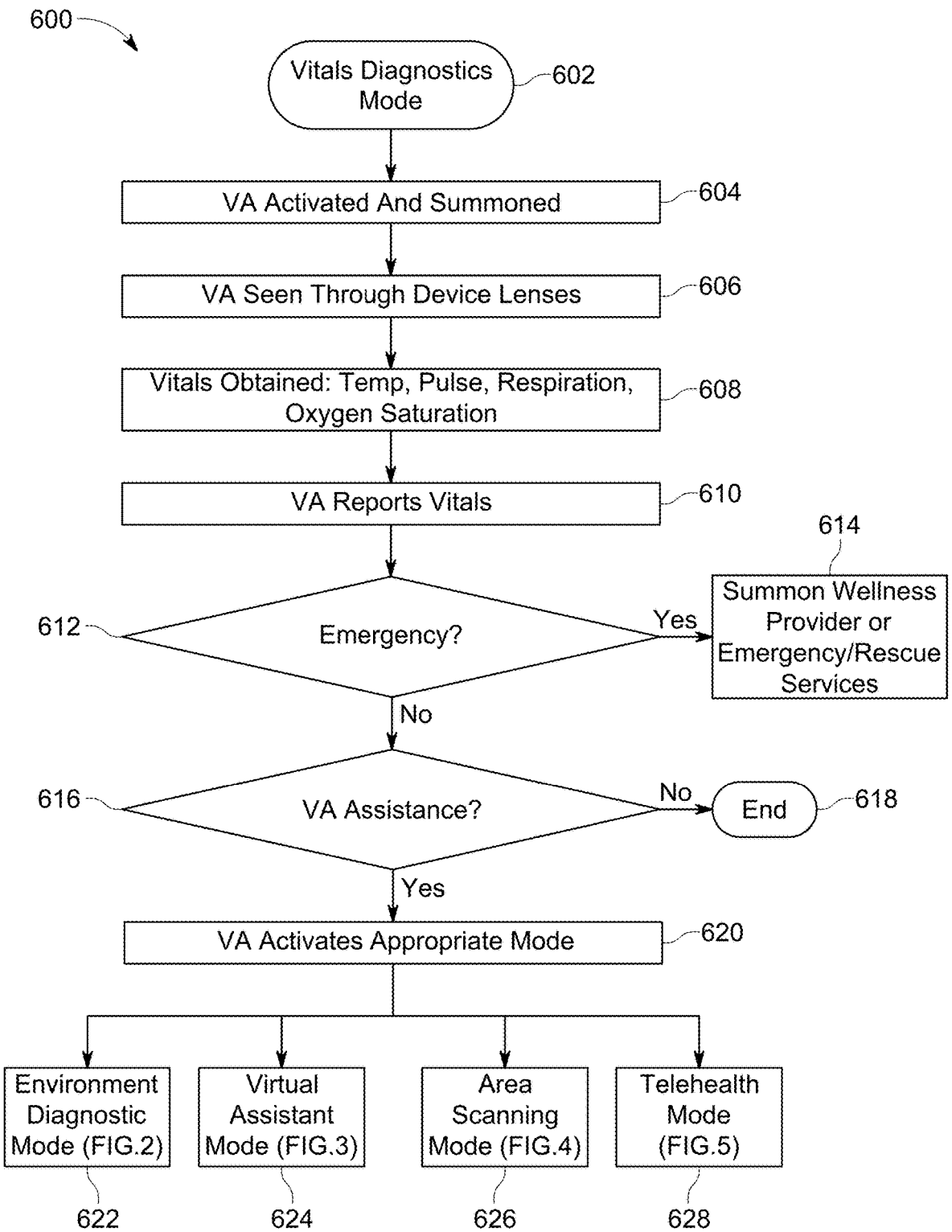
FIG. 6 is a flow chart illustrating a vitals diagnostics mode of the interactive medical communication device of FIG. 1, according to this disclosure.

FIG. 5 is a flow chart illustrating telehealth mode 500 of interactive medical communication device 10, according to this disclosure. In one non-limiting example, telehealth mode 500 is initiated in step 502 by actuation of left hinge button 48 ("omega link"). Telehealth mode 500 may alternatively be linked to from other operation modes of device 10, such as from area scanning mode 400 (FIG. 4; step 422) or from vitals diagnostics mode 600 (FIG. 6; step 628).

Telehealth mode 500 activates a telecommunications component of device 10 (step 504) to connect the user with their preferred wellness professional/provider or physician, or to make a recommendation for a wellness/provider or physician based on the user's preferred treatment modality. In step 506, the virtual assistant offers assistance, asking whether the user has a preferred wellness provider. If the user has a preferred wellness provider (step 508-Yes), device 10 connects to the user's preferred wellness provider. The connection may be a phone call from device 10 to the wellness provider or, if the wellness provider is a user of another interactive medical communication device 10, the connection may be a projected image/video of the wellness provider into the user's augmented or virtual reality space (step 510).

If the user does not have a preferred wellness provider (step 508-No), the virtual assistant seeks to connect the user with an appropriate wellness provider. In step 512, for example, the virtual assistant obtains the user's preferred treatment modality. For example, the user may be seeking a holistic provider, veteran's assistance, psychologist, psychiatrist, life coach, psychotherapist, substance abuse professional, health coach, plant-based operator, wellness coach, social worker, etc. In step 514, the virtual assistant recommends a wellness provider(s) in the user's chosen treatment modality. In step 516, device 10 connects to the user's chosen wellness provider. The connection may be a phone call from device 10 to the wellness provider or, if the wellness provider is a user of another interactive medical communication device 10, the connection may be a projected image/video of the wellness provider into the user's augmented or virtual reality space (step 516). As described with reference to virtual assistant mode 300, the user may connect to a network of wellness providers and support givers in real time for support. In one implementation, digital images/videos of available wellness providers and support givers may be projected into an augmented or virtual reality "room", with the virtual assistant available to introduce the user to those present in the virtual room.

FIG. 6 is a flow chart illustrating vitals diagnostics mode 600 of interactive medical communication device 10, according to this disclosure. In one non-limiting example, vitals diagnostics mode 600 is initiated in step 602 by actuation of bridge button 40 ("delta link"). Vitals diagnostics mode 600 may alternatively be linked to from other operation modes of device 10, such as from area scanning mode 400 (FIG. 4; step 424).

Vitals diagnostics mode 600 monitors and provides information pertaining to the user's vital signs and health. This may include vital signs such as, for example and without limitation, temperature, heart rate, blood pressure, pulse oxygen and oxygen saturation, hydration levels, and respiration. If needed, the user's wellness provider and/or emergency rescue services can be summoned. In step 604, the virtual assistant is activated and summoned (step 604) and can be seen by the user through lenses 12, 14 of device 10 (step 606). In step 608, the user's vital signs such as (without limitation) temperature, heart rate, blood pressure, pulse oxygen and oxygen saturation, hydration levels, and respiration are obtained. The vital signs may be obtained, for example, via data measured by sensors 62 and 64. The virtual assistant assesses and reports the vital signs to the user in step 610.

If the user's vital signs indicate that an emergency exists (step 612-Yes), the virtual assistant summons medical assistance such as the user's wellness provider or emergency/rescue services as appropriate to the user's condition (614). If the user's vital signs do not indicate an emergency (step 612-No), the user is asked whether further virtual assistance is needed. If no further assistance is needed (step 616-No), the vitals diagnostics mode is ended (step 618). If the user would like further assistance (step 616-Yes), based on the vitals diagnostics results, the virtual assistant activates the appropriate operational mode (step 620). Depending on the results of the vitals diagnostics, the virtual assistant may activate environmental diagnostics mode 200 (step 622); virtual assistant mode 300 (step 624); area scanning mode 400 (step 626); or telehealth mode 500 (step 628).

The virtual assistant may also have the ability to text the user of device 10 with helpful information or suggestions while in vitals diagnostic mode 600 or in any of the other modes of device 10. For example, if the user is consuming alcoholic beverages and sensors 62, 64 detect that the user is dehydrated, the virtual assistant may text a suggestion to the user to drink water.

Device 10 may monitor and measure additional biometrics such as, for example, the brainwaves of the user. In other words, device 10 may obtain neurofeedback from the user, which is an advanced type of biofeedback. By observing how the user's neurofeedback in response to situations that they are exposed to, such as a trauma or stressful situation, a simulation can be created to relax and/or heal the user. The simulation may be a relaxation mode to heal the brain in response to the trauma or stressful situation, for example.

In addition to activating the modes of device 10 separately, a command or function may be provided to activate some or all modes of device 10 simultaneously, such that device 10 is carrying out multiple monitoring functions at once and continually. In other words, for example, environmental diagnostics mode 200, virtual assistant mode 300, area scan mode 400 and vitals diagnostic mode 600 may all be activated and carried out simultaneously, rather than carried out separately, such that device 10 is monitoring everything that goes on within and around the user.

Figure 7:
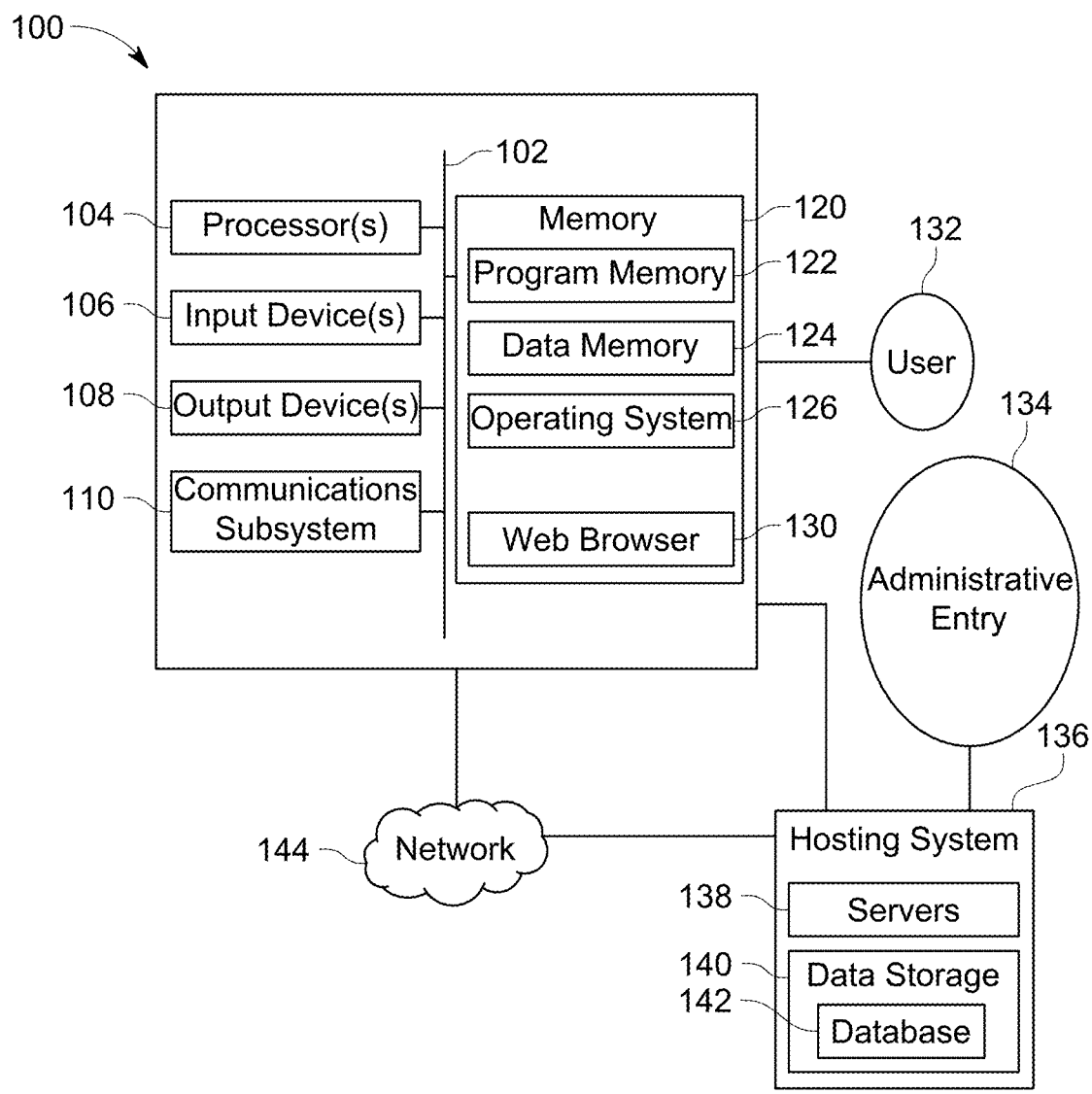
FIG. 7 is a conceptual block diagram illustrating a system of one or more computing devices for implementing the interactive medical communication device and methods of FIGS. 1-6, according to this disclosure.

Device 10 comprises suitable computing components for carrying out the various functions of device 10, including the methods of FIGS. 2-6. In one non-limiting example, some or all of the computing components of device 10, described with reference to FIG. 7, are disposed in the right and/or left temples 22, 24 of device 10. In particular, one or more processors 104 receive input signals from one or more input devices 106 (e.g., lenses, input buttons, sensors, microphones), execute instructions stored in memory 120, and output signals to one or more output devices 108 (e.g., display, speakers).

FIG. 7 illustrates an exemplary, non-limiting system of one or more computing devices 100 and various components that may be employed in practicing embodiments of this disclosure. Computing device 100 may be any type of computing device known or created in the future. This may include, without limitation, fixed in place computers, such as desktop computers or mobile computing devices. Mobile computing devices may include, but are not limited to, laptop computers, smartphones and mobile phones, tablets, wearable devices, smart watches, or any other type of mobile electronic, computing device. Moreover, although device 10 has been described primarily as being embodied in eyeglasses, it should be understood that device 10 could be embodied in other wearable devices such as, without limitation, clothing, jackets, watches, etc.

FIG. 7 is a schematic illustration of one embodiment of a computing device 100 that can perform and implement the methods and architectures disclosed herein, and/or can function as the host computer system, a remote kiosk/terminal, a mobile device and/or any other necessary computer system. FIG. 7 provides only a generalized illustration of components of computing device 100, any or all of which may be utilized as appropriate, and broadly illustrates how individual system elements may be implemented in a relatively separated manner or in a relatively more integrated manner.

Computing device 100 may be any type of information handling system, including, but not limited to, any type of computing device as noted above. To reiterate, this may include small handheld and/or wearable devices, such as handheld computer/mobile telephones, as well as large mainframe systems, such as a mainframe computer. Other non-limiting examples of computing devices include laptops, notebooks, workstation computers, personal computer systems, as well as servers (e.g., servers 138). Computing devices 100 can be used by various parties described herein and may be connected on a computer network, such as computer network 144. Types of computer networks that can be used to interconnect the various information handling systems may include, but are not limited to, Local Area Networks (LANs), Wireless Local Area Networks (WLANs), the Internet (e.g., World Wide Web), the Public Switched Telephone Network (PSTN), other wireless networks, and any other network topology that can be used to interconnect information handling systems.

Computing device 100 is shown comprising hardware elements that can be electrically coupled via a bus 102 (or may otherwise be in communication, as appropriate). The hardware elements of computing device 100 may include one or more processors 104, including without limitation one or more general-purpose processors and/or one or more special-purpose processors (such as digital signal processing chips, graphics acceleration processors, and/or the like). Computing device 100 may further include one or more input devices 106, such as (without limitation) camera lenses 12, 14, 50; input devices (e.g., buttons) 40, 42, 44, 46, 48; sensors 62, 64; and/or a microphone of device 10.

Computing device 100 may also include one or more output devices 108 such as a display and speakers 52, 54 of device 10. In some embodiments, an input device 106 and an output device 108 of computing device 100 may be integrated, for example, in a touch screen or capacitive display as commonly found on mobile computing devices as well as desktop computers and laptops.

Processors 104 may have access to a memory such as memory 120. Memory 120 may include one or more of various hardware devices for volatile and non-volatile storage and may include both read-only and writable memory. For example, memory 120 may comprise random access memory (RAM), CPU registers, read-only memory (ROM), and writable non-volatile memory, such as flash memory, hard drives, floppy disks, CDs, DVDs, magnetic storage devices, tape drives, device buffers, and so forth. Memory 120 is not a propagating signal divorced from underlying hardware and is thus non-transitory. Memory 120 may include program memory such as program memory 122 capable of storing programs and software, such as software application 10 and other computer or application programs. Memory 120 may also include data memory such as data memory 124 that may include database query results, configuration data, settings, user options or preferences, etc., which may be provided to program memory 122 or any element of computing device 100.

Computing device 100 may further include (and/or be in communication with) one or more non-transitory storage devices, which can comprise, without limitation, local and/or network accessible storage, and/or can include, without limitation, a disk drive, a drive array, an optical storage device, a solid-state storage device such as a random access memory ("RAM") and/or a read-only memory ("ROM"), which can be programmable, flash-updateable and/or the like. Such storage devices may be configured to implement any appropriate data storage, including without limitation, various file systems, database structures, and/or the like. The storage devices may be non-volatile data storage devices in one or more non-limiting embodiments. Further, computing device 100 may be able to access removable nonvolatile storage devices that can be shared among information handling systems (e.g., computing devices) using various techniques, such as connecting the removable nonvolatile storage device to a USB port or other connector of the information handling systems.

Computing device 100 may also include a communications subsystem 110, which may include without limitation a modem, a network card (wireless or wired), an infrared communication device, a wireless communication device and/or chipset (such as a Bluetooth™ device, an 802.11 device, a WiFi device, a WiMax device, cellular communication facilities, etc.), and/or the like. Communications subsystem 110 may permit data to be exchanged with a network (e.g., such as network 144), other computer systems, and/or any other devices.

Computing device 100 also comprises software components, shown as being located within memory 120, which may include an operating system 126, device drivers, executable libraries, and/or other code, which may comprise computer programs provided by various embodiments, and/or may be designed to implement methods, and/or configure systems as described herein. The methods and procedures of this disclosure may be implemented as code and/or instructions executable by a computer (and/or a processor within a computer). Such code and/or instructions can be used to configure and/or adapt computing device 100 to perform one or more operations in accordance with the described methods of this disclosure.

A set of these instructions and/or code might be stored on a computer-readable storage medium, such as the storage device(s) described above. In some cases, the storage medium might be incorporated within a computer system, such as computing device 100. In other embodiments, the storage medium might be separate from computing device 100 (e.g., a removable medium, such as a compact disc or USB stick), and/or be provided in an installation package, such that the storage medium can be used to program, configure, and/or adapt a general-purpose computer with the instructions/code stored thereon. These instructions might take the form of executable code, which is executable by the computing device 100 and/or might take the form of source and/or installable code, which, upon compilation and/or installation on the computing device 100 (e.g., using any of a variety of generally available compilers, installation programs, compression/decompression utilities, etc.) then takes the form of executable code.

Substantial variations may be made in accordance with specific requirements. For example, customized hardware may be used, and certain elements may be implemented in hardware, software (including portable software, such as applets, etc.), or both. Further, connection to other computing devices such as network input/output devices may be employed.

Some embodiments may employ a computer system (such as computing device 100) to perform methods in accordance with this disclosure. Some or all of the described methods may be performed by computing device 100 in response to one or more processors 104 executing one or more sequences of one or more instructions (which might be incorporated into operating system 126 and/or other code contained in memory 120). Such instructions may be read into memory 120 from another computer-readable medium, such as one or more of the storage devices. Execution of the sequences of instructions contained in memory 120 may cause one or more processors 104 to perform one or more methods described herein.

The terms "machine-readable medium" and "computer-readable medium," as used herein, refer to any medium that participates in providing data that causes a machine to operate in a specific fashion. In an embodiment implemented using computing device 100, various computer-readable media might be involved in providing instructions/code to the one or more processors 104 for execution and/or might be used to store and/or carry such instructions/code (e.g., as signals). In many implementations, a computer-readable medium is a physical and/or tangible storage medium. Such a medium may take many forms, including but not limited to, non-volatile media, volatile media, and transmission media. Non-volatile media may include, for example, optical and/or magnetic disks which may be an example of storage devices. Volatile media may include, without limitation, dynamic memory, which may be a type of memory included in memory 120. Transmission media may include, without limitation, coaxial cables, copper wire and fiber optics, including the wires that comprise the bus 102, as well as the various components of the communications subsystem 110 (and/or the media by which the communications subsystem 110 provides communication with other devices). Transmission media can also take the form of waves (including without limitation radio, acoustic, and/or light waves, such as those generated during radio-wave and infrared data communications).

Common forms of physical and/or tangible computer-readable media include, for example, a floppy disk, a flexible disk, hard disk, magnetic tape, or any other magnetic medium, a CD-ROM, any other optical medium, any other physical medium with patterns of holes, a RAM, a PROM, EPROM, a FLASH-EPROM, any other memory chip or cartridge, a carrier wave as described hereinafter, or any other medium from which a computer can read instructions and/or code.

Various forms of computer-readable media may be involved in carrying one or more sequences of one or more instructions to processor(s) 104 for execution. The instructions may initially be carried on a magnetic disk and/or optical disc of a remote computer. A remote computer might load the instructions into its dynamic memory and send the instructions as signals over a transmission medium to be received and/or executed by computer system 100. These signals, which may be in the form of electromagnetic signals, acoustic signals, optical signals, and/or the like, are all examples of carrier waves on which instructions can be encoded, in accordance with various aspects of the embodiments.

Communications subsystem 110 (and/or components thereof) generally will receive the signals, and bus 102 may then carry the signals (and/or the data, instructions, etc. carried by the signals) to memory 120, from which one or more processors 104 retrieve and execute the instructions. The instructions received by memory 120 may optionally be stored on a non-transitory storage device either before or after execution by processor(s) 104.

Computing device 100 may be in communication with one or more networks, such as network 144. Network 144 may include a local area network (LAN), such as a company Intranet, a metropolitan area network (MAN), or a wide area network (WAN), such as the Internet or World Wide Web. Network 144 may be a private network, a public network, or a combination thereof. Network 144 may be any type of network known in the art, including a telecommunications network, a wireless network (including Wi-Fi), and a wireline network. Network 144 may include mobile telephone networks utilizing any protocol or protocols used to communicate among mobile digital computing devices (e.g., computing device 100), such as GSM, GPRS, UMTS, AMPS, TDMA, or CDMA. In one or more non-limiting embodiments, different types of data may be transmitted via network 144 via different protocols. In further non-limiting other embodiments, computing device 100 may act as a standalone device or may operate as a peer machine in a peer-to-peer (or distributed) network environment.

Network 144 may further include a system of terminals, gateways, and routers. Network 144 may employ one or more cellular access technologies including but not limited to: 2nd (2G), 3rd (3G), 4th (4G), 5th (5G), LTE, Global System for Mobile communication (GSM), General Packet Radio Services (GPRS), Enhanced Data GSM Environment (EDGE), and other access technologies that may provide for broader coverage between computing devices if, for instance, they are in a remote location not accessible by other networks.

In one or more non-limiting embodiments, a computing device, such as computing device 100 may include a web browser such as web browser 130. Web browser 130 may be any type of web browser known in the art that may be used to access one or more web applications on user computing devices 100 or the like. Web applications are applications that are accessible by network 144 and may be located on the Internet or World Wide Web. Web browser 130 may include a variety of hardware, software, and/or firmware generally operative to present a web application to a user via a display device 108 (e.g., touchscreen or other type of monitor or display device) on a computing device. Examples of suitable web browsers include, but are not limited to, MICROSOFT EXPLORER, MOZILLA FIREFOX, and APPLE SAFARI. Web browser 130 may be previously installed by the manufacturer or company associated with computing device 100, or alternatively, may be downloaded onto computing device 100. Web browser 130 may be stored in a separate storage device and/or memory 120.

In one or more non-limiting embodiments, one or more aspects of the embodiments described herein may be implemented as a web service. As known in the art, a web service may be a software module or software program that is designed to implement a set of tasks that is accessible from multiple computing devices, such as computing device 100 over a network, such as network 144. One or more features may be implemented as a web service accessible using the World Wide Web as the connecting network 144, although any alternative type of network may be used. When implemented as a web service, embodiments can be searched for over network 144 using input devices 106 and can be invoked accordingly. Further, when invoked as a web service, various aspects of the embodiments would be able to provide functionality to the user who invoked that web service.

When implemented as a web service, a user may invoke a series of web service calls via requests to one or more servers 138 that are part of hosting system 136 that hosts the actual web service. In one or more non-limiting embodiments, hosting system 136 may be a cloud-based type hosting system. "Cloud-based" is a term that refers to applications, services, or resources made available to users on demand via a network, such as network 144, from a cloud computing provider's server. In one non-limiting embodiment, administrative entity 134 may be the cloud computing provider and may use servers 138 to provide access to aspects of the described embodiments.

Hosting system 136 may include data storage systems 140 that can provide access to stored data by applications running on computing devices that may be geographically separate from each other, provide offsite data backup and restore functionality, provide data storage to a computing device with limited storage capabilities, and/or provide storage functionality not implemented on a computing device such as device 100.

Hosting system 136 may be a service that can be implemented as a web service, in one or more non-limiting embodiments, with a corresponding set of Web Service Application Programming Interfaces (APIs). The Web Service APIs may be implemented, for example, as a Representational State Transfer (REST)-based Hypertext Transfer Protocol (HTTP) interface or a Simple Object Access Protocol (SOAP)-based interface. Any programming languages may be used to implement aspects of the described embodiments as a web service, including, but not limited to .Net, Java, and XML. Further, a web service may use standardized industry protocol for the communication and may include well-defined protocols, such as Service Transport, XML Messaging, Service Description, and Service Discovery layers in the web services protocol stack.

For instance, the hosting system can be implemented such that client applications (for example, executing on computing device 100) can store, retrieve, or otherwise manipulate data objects in hosting system 136. Hosting system 136 can be implemented by one or more server devices 138, which can be implemented using any type of computing device.

In one or more non-limiting embodiments, administrative entity 134 is the provider and creator of certain aspects of the described embodiments. Administrative entity 134 may provide an application programming interface for use by users 132. Administrative entity 134 may be able to manipulate and alter the interface to affect its operation and maintenance on server(s) 138 and as stored on one or more data storage devices 140 that are part of hosting system 136. Data storage devices 140 included for storing data associated with the described embodiments may include one or more databases 142 that store live and historical data. Data storage devices 140, via databases 142 in some cases, may be able to store all data obtained from users 132. While administrative entity 134 is depicted as a single element communicating over network 144 and through hosting system 136, administrative entity 134 may alternatively be distributed over network 144 in multiple physical locations.

Various aspects of this disclosure may be implemented as a downloadable software module that can be stored directly on a computing device, such as computing device 100, rather than acting as a web service accessible through a computing device's web browser 130. Accordingly, user 132 may be able to download and store aspects of the described embodiments on computing device 100 as a computer-based application and software module that runs using the working engines and modules on the computing device. Some aspects of the embodiments may be preinstalled on computing device 100 or any other computing device. Aspects of the embodiments may be innate, built into, or otherwise integrated into existing platforms such as, without limitation thereto, a website, third-party program, iOS™, Android™ or any other platform capable of transmitting, receiving, and presenting data.

The methods, systems, and devices disclosed herein are examples. Various embodiments may omit, substitute, or add various procedures or components as appropriate. In alternative configurations, the methods described may be performed in an order different from that described, and/or various stages may be added, omitted, and/or combined. Also, features described with respect to certain embodiments may be combined in various other embodiments. Different aspects and elements of the embodiments may be combined in a similar manner. Technology evolves and, thus, many of the elements are examples that do not limit the scope of the disclosure to those specific examples.

Specific details are given in the description to provide a thorough understanding of the embodiments. However, embodiments may be practiced without these specific details. For example, well-known circuits, processes, algorithms, structures, and techniques have been shown without unnecessary detail to avoid obscuring the embodiments. This description provides example embodiments only, and is not intended to limit the scope, applicability, or configuration of the invention. Rather, the preceding description of the embodiments will provide those skilled in the art with an enabling description for implementing embodiments of the invention. Various changes may be made in the function and arrangement of elements without departing from the spirit and scope of the invention. Accordingly, additional components known to one of ordinary skill in the art, even if not illustrated in FIG. 7, may also be included in computing device 100.

Some embodiments are described as processes depicted as flow diagrams or block diagrams. Although each may describe the operations as a sequential process, many of the operations can be performed in parallel or concurrently. The order of the operations may be rearranged. A process may have additional steps not included in the figure. Furthermore, embodiments of the methods may be implemented by hardware, software, firmware, middleware, microcode, hardware description languages, or any combination thereof. When implemented in software, firmware, middleware, or microcode, the program code or code segments to perform the associated tasks may be stored in a computer-readable medium such as a storage medium. Processors may perform the associated tasks.

Various modifications, alternative constructions, and equivalents may be used without departing from the spirit of the disclosure. The above elements may be components of a larger system, wherein other rules may take precedence over or otherwise modify the application of the invention. Also, a number of steps may be undertaken before, during, or after the above elements are considered. Accordingly, the above description does not limit the scope of the disclosure.

The corresponding structures, materials, acts, and equivalents of all means or step plus function elements in the claims below are intended to include any structure, material, or act for performing the function in combination with other claimed elements as specifically claimed. This disclosure has been presented for purposes of illustration and description but is not intended to be exhaustive or limited to the form disclosed. Many modifications and variations will be apparent to those of ordinary skill in the art without departing from the scope and spirit of the invention.

The embodiments were chosen and described to best explain the principles of the invention and the practical application, and to enable others of ordinary skill in the art to understand the invention for various embodiments with various modifications as are suited to the particular use contemplated. The invention described herein may be practiced with modification and alteration within the spirit and scope of the appended claims. Thus, the description is illustrative and not restrictive of the invention.

The invention claimed is:

1. An interactive medical communication device comprising:
    an eyeglass frame comprising two rims connected by a bridge;
    first and second camera lenses held within the rims;
    a third camera lens configured in the bridge and configured to target objects in a field of view of the third camera lens;
    the first and second camera lenses and the third camera lens working in concert for
        projection of a digitized display of a person, object, image or video recording into an augmented or virtual reality digital space in a field of vision of a user; and
        scanning and capturing of an image of the user for projection into an augmented or virtual reality digital space of another interactive medical communication device;
    one or more memories including processor readable instructions stored thereon; and
    one or more processors configured to read the processor readable instructions to cause the interactive medical communication device to implement interactive medical communication modes, the interactive medical communication modes comprising:
    an environmental diagnostics mode for detecting and analyzing conditions in an environment around the user;
    a virtual assistant mode for displaying a virtual assistant that provides assistance to the user, wherein the virtual assistant is a digitized avatar that is displayed in the augmented or virtual reality digital space and that is capable of two-way communication with the user, the virtual assistant mode comprising:
        listening to keywords and syntax of the user;
        determining a state of mind and a thought management process of the user from the keywords and the syntax of the user; and
        offering suggestions via seamless two-way communication with the user based on the determined state of mind and thought management process of the user;
    an area scanning mode for analyzing and providing information to the user about objects in a field of vision of the user;
    a telehealth mode for connecting the user to a preferred wellness provider by:
        connecting the user to the preferred wellness provider in real time by connection to another interactive medical communication device of the preferred wellness provider;
        scanning, capturing, and projecting the image of the user into the augmented or virtual reality digital space of the another interactive medical communication device; and
        projecting an image of the preferred wellness provider as scanned and captured by the another interactive medical communication device into the augmented or virtual reality digital space in the field of vision of the user; and
    a vitals diagnostics mode for measuring vital signs of the user.

2. The interactive medical communication device of claim 1, wherein the environmental diagnostics mode comprises detecting hazards in the environment around the user and alerting the user to the hazards.

3. The interactive medical communication device of claim 1, wherein the virtual assistant mode comprises providing calming mechanisms selected from a group comprising breathing exercises, playing of music, providing guiding imagery, meditation, and playing pre-recorded messages.

4. The interactive medical communication device of claim 1, wherein the area scanning mode comprises:
    targeting objects that are within the field of the view of the user;
    obtaining information about the targeted objects; and
    displaying the obtained information on the targeted objects to the user.

5. The interactive medical communication device of claim 1, wherein the telehealth mode comprises:
    obtaining a preferred treatment modality of the user;
    providing a recommended wellness provider in the preferred treatment modality;
    projecting a digital image of the recommended wellness provider into the augmented or virtual reality digital space; and
    introducing the user to the recommended wellness provider by the virtual assistant in the augmented or virtual reality space.

6. The interactive medical communication device of claim 1, wherein the vitals diagnostics mode comprises:
    assessing the vital signs of the user; and
    summoning medical assistance if indicated by the vital signs of the user.

7. An interactive medical communication device comprising:
    an eyeglass frame comprising two rims connected by a bridge;
    first and second camera lenses held within the rims;
    a third camera lens configured in the bridge and configured to target objects in a field of view of the third camera lens;
    the first and second camera lenses and the third camera lens working in concert for projection of a digitized display of a virtual assistant that provides assistance to a user in an augmented or virtual reality digital space in a field of vision of the user, wherein the virtual assistant is a digitized avatar that is displayed in the augmented or virtual reality digital space and that is capable of two-way communication with the user, wherein the virtual assistant is configured to:
        listen to keywords and syntax of the user;
        determine a state of mind and a thought management process of the user from the keywords and the syntax of the user; and
        offer suggestions via seamless two-way communication with the user based on the determined state of mind and thought management process of the user;
    the first and second camera lenses and the third camera lens further working in concert to scan and capture an image of the user for projection into an augmented or virtual reality digital space of another interactive medical communication device;
    at least one environmental sensor held within the eyeglass frame and configured to provide information about an environment around the user of the device;
    at least one vital signs sensor held within the eyeglass frame and configured to provide vital signs of the user; and
    a telecommunications component configured to connect the user with a wellness provider by:

connecting the user to the wellness provider in real time by connection to another interactive medical communication device of the wellness provider;

scanning, capturing, and projecting the image of the user into the augmented or virtual reality digital space of the another interactive medical communication device; and projecting an image of the wellness provider as scanned and captured by the another interactive medical communication device into the augmented or virtual reality digital space in the field of vision of the user.

8. The interactive medical communication device of claim 7, wherein the virtual assistant is configured to:

provide calming mechanisms selected from a group comprising breathing exercises, playing of music, providing guiding imagery, meditation, and playing pre-recorded messages.

9. The interactive medical communication device of claim 7, wherein the device is configured to detect hazards in the environment around the user based on the information provided by the at least one environmental sensor and to alert the user to the hazards.

10. The interactive medical communication device of claim 7, wherein the device is configured to obtain information about the objects targeted by the targeting lens and to display the information about the targeted objects to the user.

11. A method for interactive medical communications in a wearable device comprising an eyeglass frame comprising two rims connected by a bridge; first and second camera lenses held within the rims; a third camera lens configured in the bridge and configured to target objects in a field of view of the third camera lens; the first and second camera lenses and the third camera lens working in concert for projection of a digitized display of a person, object, image or video recording into an augmented or virtual reality digital space in a field of vision of a user, and for scanning and capturing of an image of the user for projection into an augmented or virtual reality digital space of another interactive medical communication device; the method being implemented by one or more memories having processor readable instructions stored thereon, and one or more processors configured to execute the processor readable instructions, the method comprising:

detecting and analyzing conditions in an environment around the user;

displaying a virtual assistant that provides assistance to the user of the wearable device, wherein the virtual assistant is a digitized avatar that is displayed in the augmented or virtual reality digital space and that is capable of two-way communication with the user, and wherein the virtual assistant:

listens to keywords and syntax of the user;

determines a state of mind and a thought management process of the user from the keywords and the syntax of the user; and offers suggestions via seamless two-way communication with the user based on the determined state of mind and thought management process of the user;

analyzing and providing information to the user about objects in a field of vision of the user of the wearable device;

connecting the user of the wearable device to a wellness provider by:

connecting the user to the wellness provider in real time by connection to another interactive medical communication device of the wellness provider;

scanning, capturing, and projecting the image of the user into the augmented or virtual reality digital space of the another interactive medical communication device; and projecting an image of the wellness provider as scanned and captured by the another interactive medical communication device into the augmented or virtual reality digital space in the field of vision of the user; and measuring vital signs of the user.

12. The method of claim 11, further comprising:

providing calming mechanisms selected from a group comprising breathing exercises, playing of music, providing guiding imagery, meditation, and playing pre-recorded messages.

13. The method of claim 11, further comprising:

assessing the vital signs of the user; and summoning medical assistance if indicated by the vital signs of the user.

14. The interactive medical communication device of claim 1, wherein the area scanning mode further comprises:

continuously recording audio and video in the field of vision of the user such that life experiences of the user are recorded.

15. The interactive medical communication device of claim 7, wherein the interactive medical communication device is configured to:

continuously record audio and video in the field of vision of the user such that life experiences of the user are recorded.

16. The interactive medical communication device of claim 1, further comprising prisms configured in the eyeglass frame to assist the first and second camera lenses and the third camera lens in scanning and capturing the image of the user by capturing, redirecting, and focusing light.

17. The interactive medical communication device of claim 16, further comprising:

a right temple joined by a right hinge to a right rim of the rims and extending to a right temple tip;

a left temple joined by a left hinge to a left rim of the rims and extending to a left temple tip;

a bridge button configured in the bridge for actuating the vitals diagnostic mode;

a right temple button configured in the right temple tip for actuating the environmental diagnostics mode;

a left temple button configured in the left temple tip for actuating the virtual assistant mode;

a right hinge button configured adjacent to the right hinge for actuating the area scanning mode; and a left hinge button configured adjacent to the left hinge for actuating the telehealth mode.

* * * * *